United States Patent [19]
Saunders et al.

[11] Patent Number: 5,208,161
[45] Date of Patent: May 4, 1993

[54] FILTER UNITS

[75] Inventors: Anthony J. Saunders, Weybridge, England; Roy L. Manns, Marshfield Hills, Mass.

[73] Assignee: Polyfiltronics N.A., Inc., Rockland, Mass.

[21] Appl. No.: 465,142

[22] PCT Filed: Aug. 25, 1988

[86] PCT No.: PCT/GB88/00700
§ 371 Date: Feb. 26, 1990
§ 102(e) Date: Feb. 26, 1990

[87] PCT Pub. No.: WO89/01966
PCT Pub. Date: Mar. 9, 1989

[30] Foreign Application Priority Data

Aug. 27, 1987 [GB] United Kingdom ............... 8720253
May 17, 1988 [GB] United Kingdom ............... 8811635

[51] Int. Cl.⁵ ............... G01N 33/53; B01D 24/00
[52] U.S. Cl. ............... 435/286; 435/7.35; 435/310; 422/101; 422/102; 210/232; 210/323.1; 210/404; 210/416.1
[58] Field of Search ............... 435/287, 310, 803, 286, 435/7.35; 210/232, 323.1, 406, 416.1; 422/101, 102

[56] References Cited

U.S. PATENT DOCUMENTS

| | | | |
|---|---|---|---|
| 3,730,352 | 5/1973 | Cohen et al. | 210/406 |
| 3,907,505 | 9/1975 | Beall et al. | 422/102 |
| 3,956,125 | 5/1976 | Strutt et al. | 210/406 |
| 3,986,960 | 10/1976 | Wire et al. | 210/232 |
| 4,255,522 | 3/1981 | Fusenig et al. | 422/102 |
| 4,304,865 | 12/1981 | O'Brien et al. | 435/310 |

FOREIGN PATENT DOCUMENTS

86-07606 12/1986 PCT Int'l Appl.

OTHER PUBLICATIONS

Cole Parmer ('85–'86) p. 179.
Fisher '86 p. 736.
Webster's 9th New Collegiate Dictionary p. 808.

Primary Examiner—James C. Housel
Assistant Examiner—N. Bhat
Attorney, Agent, or Firm—Schiller & Kusmer

[57] ABSTRACT

An assay filter unit where the filter of the unit is sealed into the body of the unit to prevent any passage of material to be assayed round the edge of the filter but is removable by breaking out a filter support grid along a predetermined line of weakness, together with the filter, for assay of material retained on the filter.

10 Claims, 4 Drawing Sheets

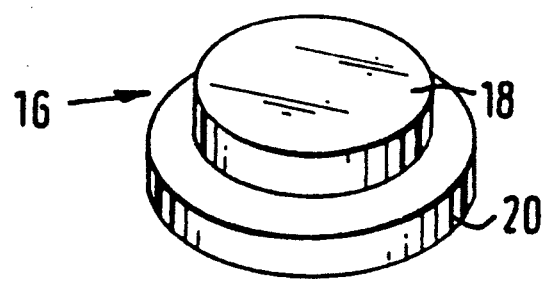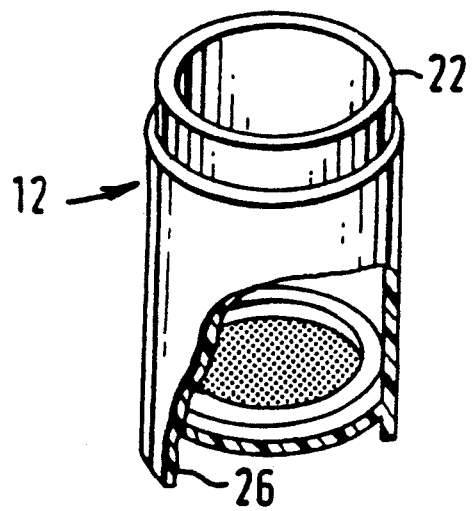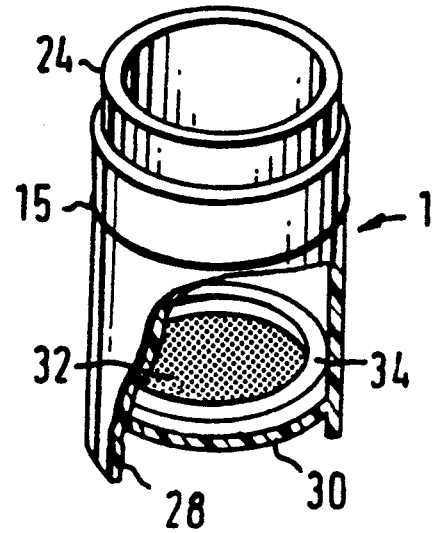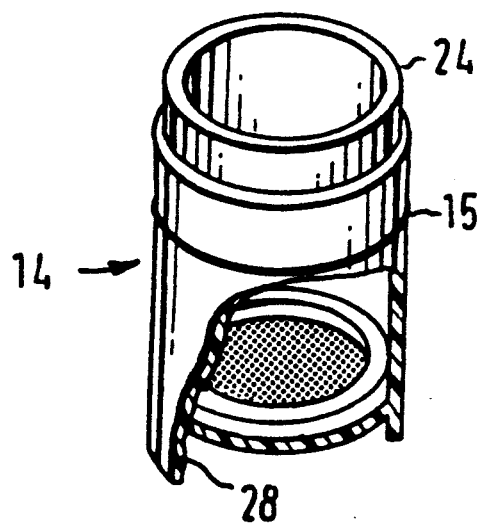
FIG. 1
FIG. 2

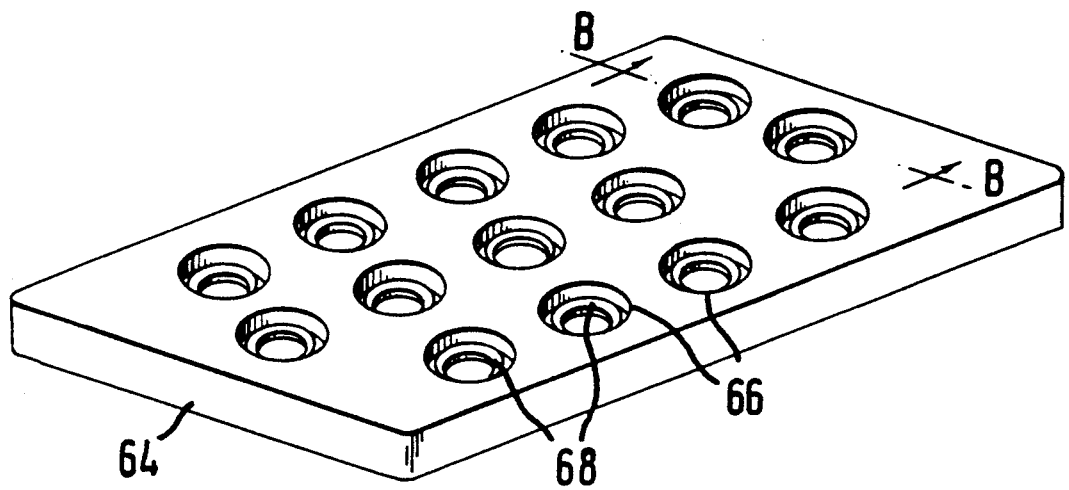
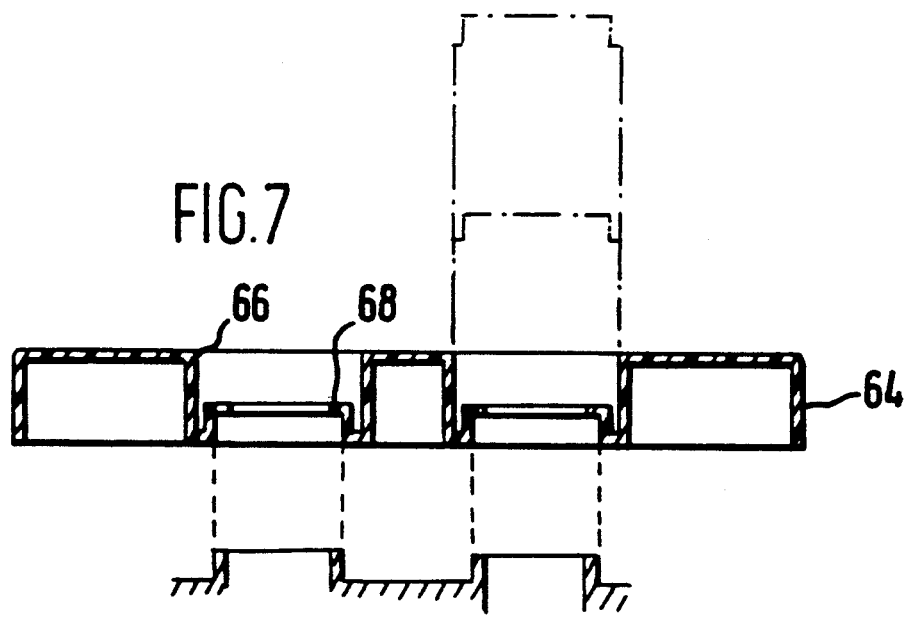

FILTER UNITS

This invention relates to the preparation of samples for assay where filtration and ready access to material retained are required.

In particular the invention addresses the need for many assays to be routinely, quickly and simply carried out in an inexpensive way and where therefore filtration equipment that is complicated and expensive to make and use will not serve.

With these requirements in mind the invention provides an assay filter unit having single or multiple filter stations and a filter at the or each station, characterised in that the filter of the or each station is sealed into the body of the unit to prevent any passage of material to be assayed round the edge of the filter but is removable by breaking out together with the filtering area of the filter the central portion of a filter support grid lying below the filter, along a predetermined line of weakness in the grid, for assay of material retained on the filter.

Such units may be used if desired in filtration assemblies comprising the assay filter unit and corresponding pre-filter unit(s), stacked for passage of filtrate from the pre-filter unit(s) to the assay filter unit.

As noted, the assay filter units may be single or in multi-station form, for example a multi-station block used alone or with separate pre-filter units.

Conveniently the line of weakness is provided by notches of vee or other stress-concentrating form (as seen insection axially of the filter station) formed in elements of the grid at its periphery.

For ease of production and use it is preferred that the body of the assay unit and the grid are integrally formed of plastics by injection moulding and the axial thickness of the elements of the grid at the notches is 0.15 to 0.5 mm, desirably 0.2 to 0.3 mm, thereby allowing both for ready flow of material during moulding and for ready breaking out of the grid after use.

Conveniently the assay filter unit, of plastics, has a plastics ring clamping the filter against the periphery o the support grid, welded (particularly ultrasonically welded) in place. In this construction it is desirable that the assay filter unit body and the ring where they abut the filter have a surface roughness of up to 0.5 microns to improve grip on the filter. Such roughness can be given by controlled sand blasting of the appropriate parts of injection moulds in which the units and rings are to be produced, and the grip it gives leads to the filter breaking out cleanly with the grid.

The invention further provides, for use with the single filter station units, a suction manifold having a plurality of stations for reception of a corresponding number of units and an anvil over which, successively, the body of each unit can be placed to break out the support grid.

In a particular application the invention may provide filtration assemblies as above for carrying out a microbiological assay for detecting a predetermined microorganism or cell in a sample containing particles larger than the predetermined microorganism or cell, each assembly including at least one first filter unit (pre-filter unit) including an open container with a filter having pores large enough to permit the passage therethrough of the predetermined microorganism or cell and small enough to prevent the passage therethrough of the particles larger than the predetermined microorganism or cell, and at least one second filter unit (assay filter unit), vertically interstackable with its respective first such unit, including an open container with a filter having pores large enough to permit the passage therethrough of aqueous liquid and small enough to retain the predetermined microorganism or cell, the filter of the or each second filter unit being, as before, sealed into the unit by a retaining ring or other means preventing any passage of material round the edge of the filter but removable from the unit by breaking out, along a predetermined line of weakness, a filter support lying below the filter, in order to conduct assay.

In such an application as many successively smaller-pore pre-filter units can be stacked as are needed to remove particulates from a particular sample without clogging the filters. For example, the assembly may include one or more third filter units (additional pre-filter units), one on top of each first filter unit, each third filter unit including a filter having pores larger than the pores of the filter of the succeeding pre-filter unit and small enough to prevent the passage therethrough of a portion of the particles in the sample larger than the predetermined microorganism or cell.

The area of the filter of pre-filter units where used should be large enough that the likelihood of clogging by the particles to be retained is small. A convenient area is 20 $mm^2$ to 500 $mm^2$. The area of the filter of the or each assay filter unit should correspondingly be large enough to prevent clogging by particles, in any reasonable sample, approximating the size of or smaller than the predetermined microorganism or cell, but small enough to concentrate the predetermined microorganism or cell conveniently for assay.

Usually, the units are cylindrical but in other embodiments, for example, the pre-filter unit is conical, its filter matching the size of the filter of the corresponding assay filter unit, allowing larger samples to be handled readily.

Other convenient optional features are that pre-filter units where used are of different colours to the assay filter units and that the assay filter units are transparent, with a fill line indicating amounts of reagents to be added in course of the assay.

Suitably the units are injection moulded, for which materials such as polypropylene, polystyrene, acrylic or modified acrylic or polyvinylchloride plastics are suitable. Filters of any convenient material and pore size can be used in the units, made for example from cellulose acetate, nylon, or nitrocellulose. The size and shape of the units may of course be varied to meet the requirements of varying sample characteristics, including concentration and size of particulate matter, and concentration and size of the microorganism or cell of interest.

In a particular embodiment the assay filter unit has a recessed base below the filter, and is used with a reversible cap having a first portion and a second portion, the perimeter of the first portion being smaller than the perimeter of the second portion, the second portion being adapted to fit snugly on top of the unit or, optionally, any pre-filter unit and the first portion being adapted to fit snugly into the recessed base to provide a leak-proof closure.

For use with microorganisms, the filter of the assay filter unit conveniently has pores of 0.02 to 3 microns diameter; the filter of any pre-filter unit then has pores of a diameter 1 to 50 microns.

The units may for example be adapted to test a diluted sample having a volume of 1 ml upwards, e.g. to 50 ml. according to the number of units. Small volumes apply for example to a standard 96 well unit, larger volumes where fewer stations are involved.

In preferred form the units of the invention can provide many advantages separately or together. Thus an assembly of assay filter and pre-filter units can permit the removal of large particulate matter during the same vacuum filtration step in which the microorganisms or cells of interest are deposited on the filter, the assembly eliminating the need for transfer of the microorganisms or cells before processing of the sample can begin. All of the filter units can be disposable, eliminating the need for the washing and sterilizing steps required for example in reusable hybridization assay apparatus. Snug fit between units can be provided, preventing leakage or accidental disassembly during use. Colour coding of units can facilitate assembly and prevent accidental reversal of like-sized filter units. A suitably rigid grid on the second (assay) filter unit, and the ring above the filter, can provide support for a fragile filter, protecting it from deformation during suction. A fill line on a transparent assay filter unit can permit easy addition of solution from, e.g., a squeeze applicator bottle, obviating time-consuming measurement of reagents. A reversible cap can be placed on any same-sized filter unit to prevent drying and contamination of the sample with airborne contaminants. The same cap if suitably designed can be reversed and used as a base for a suitably dimensional assay filter unit to prevent leakage during steps of the assay carried out before breaking out the filter. A manifold, or if desired a manifold cover applied to the manifold itself only when ready for suction, can hold a number of units containing multiple and/or duplicate samples, which can all be processed at the same time. Such a manifold cover an also serve as a convenient tray for holding the units steady while they are being loaded with samples, and for carrying them about.

Uses in particular include assay for bacteria of the genus Salmonella but many other uses applicable to food samples, to human or veterinary body fluid or other samples, and to other materials exist.

Other features and advantages of the invention will be apparent from the following description of particular embodiments thereof.

BRIEF DESCRIPTION OF THE DRAWINGS

FIG. 1 is an isometric view, partially broken away, of the parts of a particular assembly, with reversible cap;

FIG. 2 is an isometric view, partially broken away, of the assay filter unit of said assembly, which may of course also be used alone;

FIG. 6 is a view of a suction manifold cover;

FIG. 7 is a sectional elevation on B-B of FIG. 6 showing part of a suction manifold and, in outline, a filtration assembly in place.

Referring to FIG. 1, a multiple-unit assembly includes first (pre) filter unit 12, second (assay) filter unit 14, and reversible cap 16, including top portion 18 and bottom portion 20.

Figure 3:
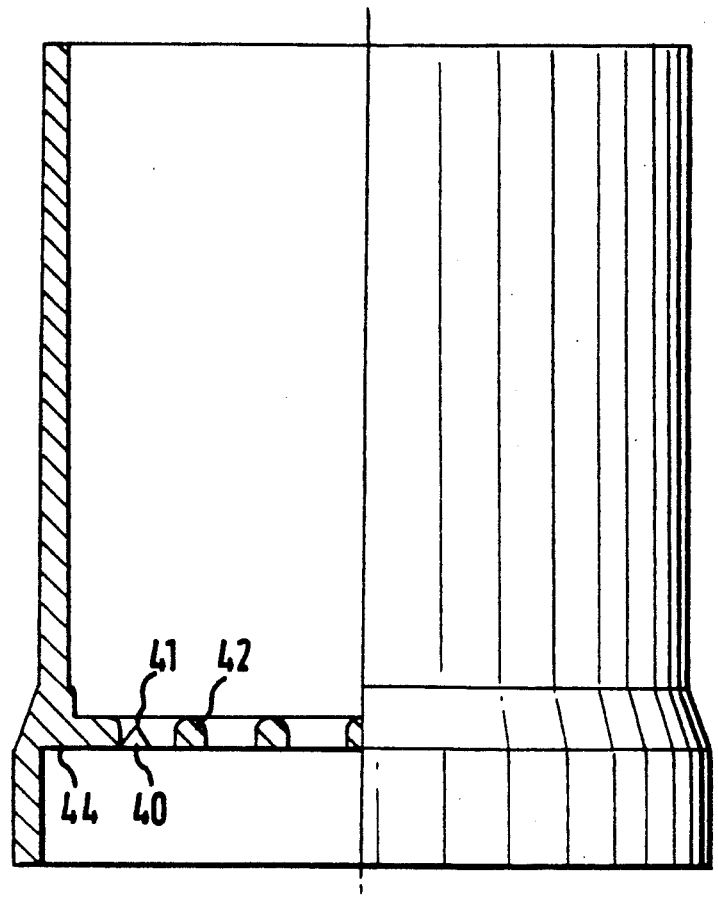
FIG. 3 is a part-sectional elevation of the body of a further assay filter unit.

The container of unit 12 is of blue injection-molded polypropylene, and the container of unit 14 is transparent polypropylene. Container 14 bears circumferential fill line 15.

Each of units 12 and 14 has a rim portion, 22 and 24, which fits into the recessed portion 26 of the unit above it, or into bottom portion 20 of cap 16. Top portion 18 of cap 16 alternatively fits snugly into recessed portion 28 of unit 14. Each unit is approximately 2.5 cm high from recess to rim, and has a volume of about 50 ml.

As is best shown in FIG. 2, each filter unit (designated 1) includes support 30, filter 32, and filter holddown ring 34. Support 30 is injection moulded integral with unit 1 and has a circumferential border surrounding a grid. The border is wide enough to provide a continuous surface against which the top surface of a rim of a lower filter unit can abut without being so wide as to interfere with the passage of the filtrate. The grid may be of any open pattern so long as the overlying filter is supported and sufficient space is allowed for passage of the filtrate but the preferred form is that of FIG. 4.

Filter 32, overlying support 30 and held down by ring 34, is the primary functional portion of the unit. The pore size of filter 32 depends on the unit's purpose. The filter of unit 12 (FIG. 1) has for example pores sufficiently large to allow a microorganism of interest (e.g. Salmonella) to pass through but sufficiently small to retain larger bacteria and particulates. The filter 32 of unit 14 is a filter membrane which retains the microorganism and which is suitable for use in the assay.

Filter 32, as mentioned above, is secured within unit 1 by means of ring 34, which is thermally or ultrasonically welded into the unit to form a complete seal.

Figure 4:
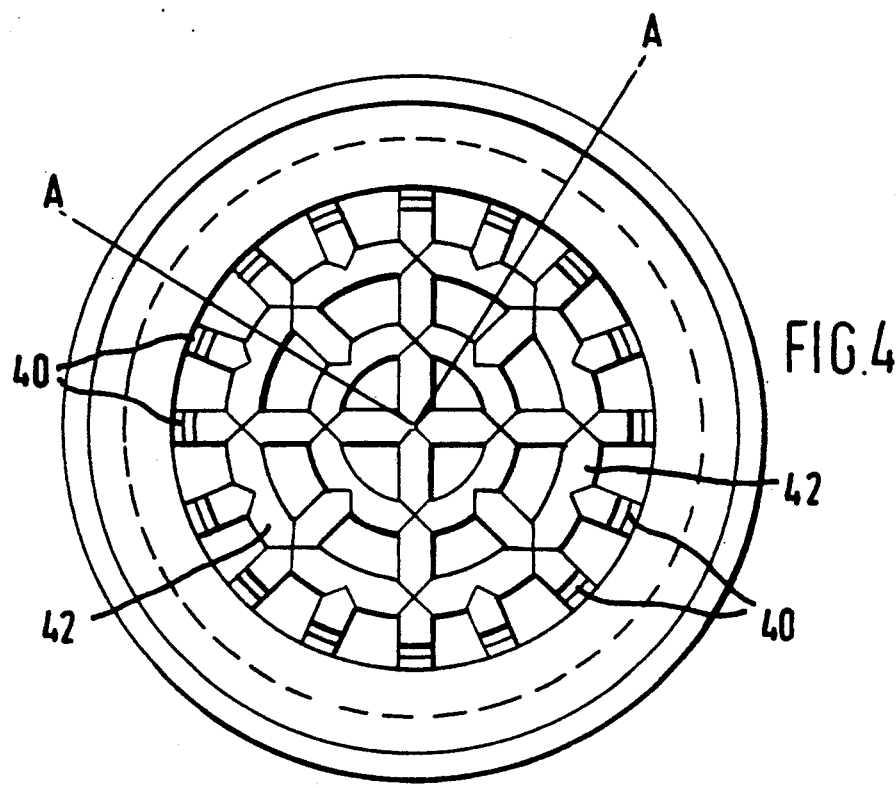
FIG. 4 is an underneath plan view of said body showing at A—A the section line of FIG. 3.

The details of the grid are seen in FIGS. 3 and 4. It is approximately one and one quarter mm in thickness axially of the unit with a 60° included-angle vee notch 40 moulded into each element 42 of it, leaving a web thickness, at 41 and as measured axially of the unit, of one quarter mm. This web allows for flow of material during moulding and is both strong enough to withstand handling and filtration suction pressures and weak enough to break out easily against an anvil under manual pressure only. The upper faces of the grid elements 42 are rounded to support filter 32 without risk of rupture and also to increase the effective free filter area. The form of the grid is seen in FIG. 4 and is designed for maximum support with minimum interference with flow, especially important when small pore size filters are in use.

Figure 5:
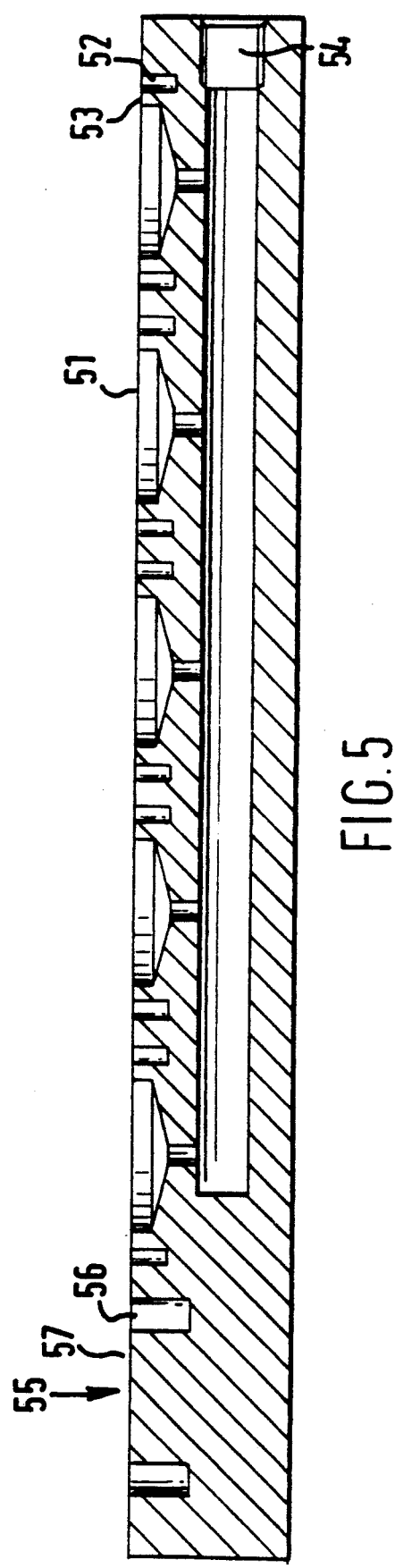
FIG. 5 is a sectional view of a suction manifold.

The manifold of FIG. 5 is designed to receive filtration assemblies, or assay filter units alone, specifically those of FIGS. 3 and 4 at five stations 51. The base portion of the body of a given filter unit fits into one of the annular recesses 52 of the manifold, with annular land 53 contacting the unit within the base of the unit at 44. Suction applied through bore 54 then draws filtrate from a sample placed in a (or an uppermost) pre-filter unit into the assay filter unit and then through the assay filter to waste, leaving the organism or other material to be assayed on the filter of the assay unit. Unused stations, or assemblies or units filtering faster than others, can be covered with caps 16 if required. When filtration is complete, (and it will be appreciated that according to the design of the assemblies and the application, it may be by centrifugation rather than suction), any pre-filter units are discarded and any washing or reagent treatments required using filtration may be carried out. Then the assay filter units are transferred in turn to anvil station 55 where they fit in annular recess 56. Anvil 57 is sharp edged and dimensioned to press out the grid and overlying filter, breaking the grid out at the apex of notches 40 and passing internally of ring 34. Only hand pressure is required and the filter may be dropped directly from the body of the unit into a receptacle for further treatment. The unit itself and the broken grid are discarded.

In a particular application, the filtration assembly is used to prepare food samples for a nucleic acid hybridization assay for Salmonella bacteria For example, filter 32 (FIG. 2) of filter unit 12 (FIG. 1) is a microporous polymeric membrane having pores of nominal diameter 1 to 50 microns. These pore sizes are large enough to allow the passage therethrough of Salmonella bacteria and small enough to retain larger bacteria and large food particles The diameter of this filter is approximately 2.4 cm, providing an area large enough to prevent clogging by particles of a typical food sample diluted 10:1 with water.

The filter of unit 14 has pores of 0.2 to 3 microns, small enough to retain Salmonella bacteria and large enough to allow the passage of aqueous liquid. The diameter of the filter is 2.4 cm, providing an area large enough to prevent clogging by the Salmonella-sized and smaller particles which are present in some food samples (e.g. flour and peanut butter) and small enough to provide a high enough concentration of Salmonella bacteria on at least a portion of the filter to render the hybridization assay straightforward.

Referring now to FIGS. 6 and 7, a manifold cover 64 of injection-molded polystyrene, contains a plurality of cylindrical wells 66. Lip 68 in each of wells 66 prevents the units from extending through manifold cover 64. The cover fits over a manifold base of cast epoxy (FIG. 7), which fits a conventional vacuum-suction device (not shown).

A sample of food to be tested for Salmonella is diluted 10 fold with water and poured into unit 12 (FIG. 1); the assembly is at this point assembled and resting on one of the wells of manifold cover 64. Vacuum is applied, causing liquid and small particles, including Salmonella, to pass through the filter of unit 12, while larger bacteria and food particles are retained Unit 12 is then discarded.

Prehybridization buffer (of conventional formula) is then added to unit 14, up to fill line 15. Vacuum is again applied. Hybridization buffer, including a labelled probe is then added and unit 14 is removed from the manifold, cap 16 is inserted in recess 28, and the unit is incubated at 37° for 2 hours. The filter support is then broken out and the filter removed, and labelled complexes are then detected as an indication in the sample of Salmonella bacteria.

I claim:

1. An assay filter unit for filtering a sample and comprising, in combination:

a body having an internal passageway:
   a filter disposed within said passageway;
   a filter support means for supporting said filter and seal within said body so as to prevent passage of any of said sample around the edges of said filter, and provided with a line of mechanical weakness disposed peripherally about said support means so that said filter is removable from said body by breaking said support means along said line.

2. A filter unit according to claim 1 wherein said filter support means is a grid and said line of weakness is formed, at least in part, by notches of stress-concentrating form in elements of said grid.

3. A filter unit according to claim 2 wherein said body and said grid are integrally molded together of synthetic polymer.

4. A filter unit according to claim 3 wherein the axial thickness of said grid at said notches is predetermined to allow for both ready flow of material during molding and for ready breaking out of the grid after use.

5. A filter unit according to claim 4 wherein said axial thickness at said notches is in the range of about 0.15 to 0.5 mm.

6. A filter unit according to claim 4 wherein said axial thickness at said notches is in the range of about 0.2 to 0.3 mm.

7. A filter unit according to claim 1 wherein said unit is formed of synthetic polymer and includes a ring clamping said filter against the periphery of said support grid and welded in place.

8. A filter unit according to claim 7 wherein said body and said ring, where they abut said filter, have surfaces of roughness sufficient to improve the grip on said filter.

9. A filter unit according to claim 1 wherein disposed within a suction manifold having a plurality of stations for receiving a corresponding number of similar units, and an anvil over which, successively, said body of each said unit can be placed to break out the corresponding said grid along the corresponding line of weakness.

10. A filtration assembly, comprising, in combination, a plurality of assay units, each comprising:

a body having an internal passageway:
    a filter disposed within said passageway;
    a filter support means for supporting said filter and seal within said body so as to prevent passage of any of said sample around the edges of said filter, and provided with a line of mechanical weakness disposed peripherally about said support means so that said filter is removable from said body by breaking said support means along said line;
    said units being stacked for passage of filtrate therethrough from one to successive units.

* * * * *